United States Patent [19]

Langhorst

[11] Patent Number: 4,612,019

[45] Date of Patent: Sep. 16, 1986

[54] METHOD AND DEVICE FOR SEPARATING WATER VAPOR FROM AIR

[75] Inventor: Marsha L. Langhorst, Midland, Mich.

[73] Assignee: The Dow Chemical Company, Midland, Mich.

[21] Appl. No.: 400,819

[22] Filed: Jul. 22, 1982

[51] Int. Cl.[4] .............................................. B01D 53/22
[52] U.S. Cl. ........................................ 55/16; 55/30; 55/35; 55/158; 55/275; 55/387
[58] Field of Search ................. 55/16, 30, 35, 74, 158, 55/275, 387

[56] References Cited

U.S. PATENT DOCUMENTS

| 3,198,335 | 8/1965 | Lewis et al. | 210/321 |
|---|---|---|---|
| 3,307,330 | 5/1967 | Niedzielski et al. | 55/16 |
| 3,367,850 | 2/1968 | Johnson | 204/1 |
| 3,422,008 | 1/1969 | McLain | 210/22 |
| 3,705,480 | 12/1972 | Wireman | 55/275 |
| 3,735,558 | 5/1973 | Skarstrom et al. | 55/16 |
| 3,751,879 | 8/1973 | Allington | 55/158 |
| 3,832,830 | 9/1974 | Gerow | 55/158 |
| 3,884,814 | 5/1975 | Vogt et al. | 210/321 |
| 3,911,080 | 10/1975 | Mehl et al. | 55/16 X |
| 3,926,561 | 12/1975 | Lucero | 23/232 |
| 3,992,153 | 11/1976 | Ferber et al. | 55/16 X |
| 4,040,805 | 8/1977 | Nelms et al. | 55/158 |
| 4,080,743 | 3/1978 | Manos | 55/16 X |
| 4,080,744 | 3/1978 | Manos | 55/16 X |
| 4,083,765 | 4/1978 | Lawson | 204/195 |
| 4,120,098 | 10/1978 | Manos | 55/16 X |
| 4,132,594 | 1/1979 | Bank et al. | 55/158 X |
| 4,199,445 | 4/1980 | Chiang et al. | 210/23 |
| 4,207,192 | 6/1980 | Coplan et al. | 210/321 |
| 4,208,371 | 6/1980 | Kring | 55/158 X |
| 4,269,804 | 5/1981 | Kring | 55/158 X |

FOREIGN PATENT DOCUMENTS

| 1440963 | 5/1973 | United Kingdom . | |
| 553995 | 5/1977 | U.S.S.R. | 55/275 |

OTHER PUBLICATIONS

Lowell D. White et al, "A Convenient Optimized Method for the Analysis of Selected Solvent Vapors in the Industrial Atmosphere", American Indus. Hygiene Assoc. Journal, vol. 31, Mar.–Apr. 1970, pp. 225–230.
Environmental Compliance Corporation, Catalog 103.
Skarstrom, Derwent 25313A.
Asahi Chemical Inc., Derwent 65446Y.

Primary Examiner—Robert Spitzer
Attorney, Agent, or Firm—Joe R. Prieto

[57] ABSTRACT

A device for separating water vapor from a sample of air has been developed. The device utilizes a water permeable membrane to separate the water vapor from an air stream containing other vapors, for example, organic vapors. The device is applicable, for example, in industrial hygiene applications to reduce or change humidity in an air stream prior to collection of organics on a sorbent tube.

18 Claims, 3 Drawing Figures

METHOD AND DEVICE FOR SEPARATING WATER VAPOR FROM AIR

BACKGROUND

This invention relates to a method and device for separating water vapor from air and particularly to a method and device for sampling air, for example, in the field of industrial hygiene monitoring.

Air sampling is an important function in the field of industrial hygiene. In this area, monitoring contaminant vapors in the air under actual working conditions involves collecting samples of various constituents or components in air, for example, hydrocarbons or other organics. It is known to collect such samples by drawing an air sample through a tube containing chemically adsorbent or absorbent material, for example, silica gel or charcoal, whereby the various constituents in air are collected on the adsorbent or absorbent material. Thereafter the adsorbent or absorbent material is removed from the tube. The collected constituents are desorbed, for example, with a suitable solvent and subsequently analyzed by well-known analytical methods such as liquid or gas chromatography.

Typically, the tube, also called a sorbent or sample tube, consists of a glass tube with an adsorbent or absorbent material inside the tube in a front and back section separated by a porous foam section. The front section may contain, for example, about 800 milligrams of charcoal and the back section may contain, for example, about 200 milligrams of charcoal.

When a chemical of interest passes through the front section without completely sorbing on the front section, this is known as "breakthrough". The back section serves as back-up material for collecting some of the chemical not collected in the front section. At high chemical concentrations or long sampling periods, certain chemicals usually breakthrough both sections. Breakthrough is enhanced at high humidity conditions, particularly for chemicals with poor sorption properties, for example, methyl chloride.

When significant breakthrough occurs, re-sampling is necessary to obtain an accurate analysis of the air sample and thus, much time, energy and materials are wasted.

To avoid early breakthrough, consecutive samples of certain chemicals are taken for short periods of time throughout an eight hour working day to more accurately monitor the atmosphere. Thus, an extended length of time for sampling air with a sorbent tube is not possible.

Therefore, it is desired to provide a device for separating water vapor from an air sample prior to collecting certain chemicals in air on a sorbent tube to eliminate the breakthrough problem associated with collection of the various chemicals under high humidity conditions.

It is also desired to provide a device for sampling air for a longer period of time without the occurrence of breakthrough.

SUMMARY OF THE INVENTION

The present invention is directed to a device and method for separating water vapor from air. The device comprises a casing means of water vapor impermeable material containing at least one membrane means of water vapor permeable material with a first and second side. The membrane means is positioned within the casing means to form a first and second space therein. The first and second space of the casing means communicate with each other through the wall of the membrane means. The second space of the casing means is adapted for allowing air to communicate with the first side of the membrane means. Occupying the first space of the casing means is a desiccant.

The method comprises contacting the first side of the membrane means with air containing water vapor. At least some of the water vapor contained in the air will permeate, transfer or pass through the first side to the second side of the membrane means whereby some of the water vapor is sorbed by desiccant located in the first space of the casing means.

DETAILED DESCRIPTION OF THE INVENTION

The present invention will be described hereinafter with specific reference to industrial hygiene applications and, particularly, for use as a personal monitoring device. It will be understood, however, that it is not intended to be limited to such applications. For example, the device of the present invention can be used in combination with a respirator cartridge to improve filtration of certain chemicals in the atmosphere.

Figure 1:
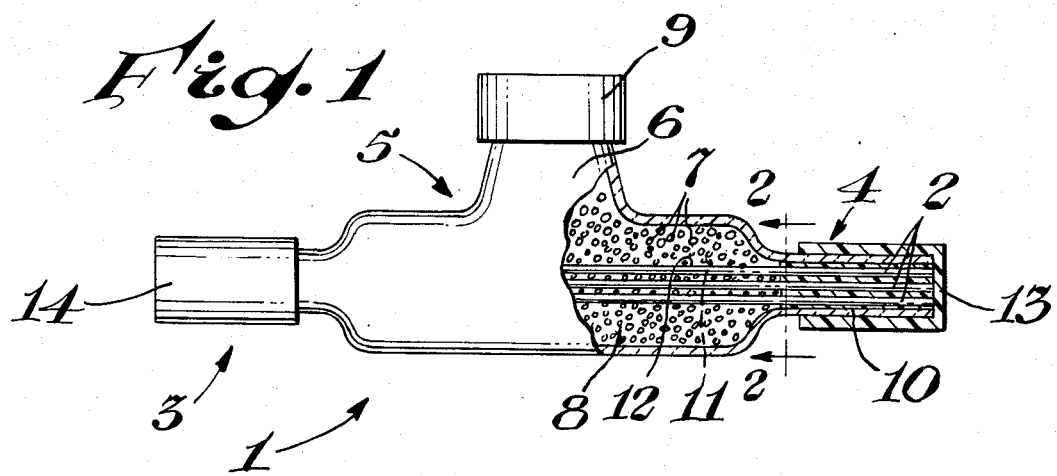
FIG. 1 is a cross-sectional view of one of the embodiments of the present invention.
Figure 2:
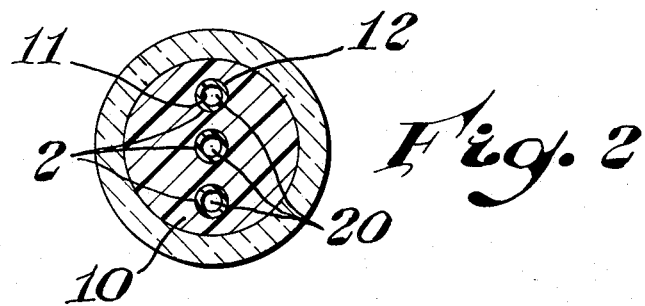
FIG. 2 is a cross-sectional view taken along lines 2—2 of FIG. 1.
Figure 3:
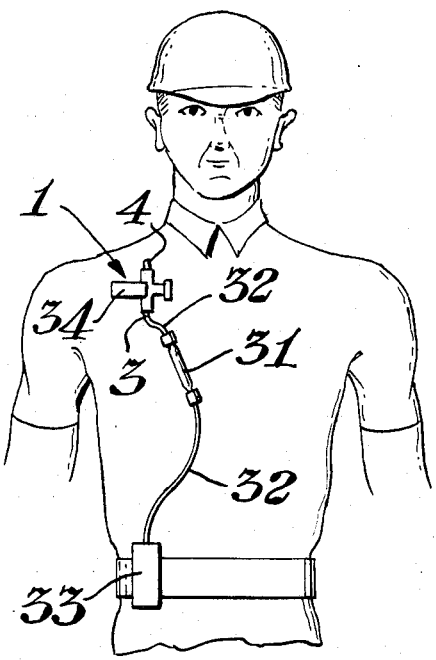
FIG. 3 is an illustration of the device used as a personal monitoring device.

One of the embodiments of the device of the present invention is illustrated in FIGS. 1, 2 and 3. Referring to FIGS. 1 and 2, a device for removing water vapor from an air sample according to the present invention is shown in the form of a cylindrical casing or housing 1 having any number of horizontally aligned hollow fiber membranes 2 extending through the axis of the casing 1. In FIGS. 1 and 2, three hollow fiber membranes 2 are shown. The casing 1 consists of three sections, two cylindrical end sections 3 and 4, and a middle cylindrical section 5. The inside diameter of the end sections 3 and 4 are smaller than the inside diameter of the middle section 5.

The middle section 5 of the cylindrical casing 1 optionally contains an opening 6 extending outwardly from the middle section 5 for introducing desiccant, for example, silica gel, in the form of small solid elements 7 into the middle section 5. The silica gel elements 7 occupy the space 8 surrounding the hollow fiber membranes 2. The opening 6 of the casing 1 can be sealed off with a removable cap 9. The hollow fiber membranes 2 are fixed into position in the casing 1 by a sealant 10, for example epoxy, at the end sections 3 and 4 of the casing 1 creating the space 8 between the outside or second side 12 of the hollow fiber membranes 2 and inner surface of the middle section 5 of the casing 1. The bores 20 of the hollow fiber membranes 2 are open to provide an inlet and outlet for air to travel through the bores 20 of the hollow fiber membranes 2 but not through space 8 of the casing 1. Water vapor contained in an air sample passing through the bores 20 of the hollow fiber membranes 2 will contact the inside or first side 11 of the hollow fiber membranes 2. The water vapor will then transfer or permeate from the first side 11 to the outside or second side 12 of the hollow fiber membranes 2 because of a concentration gradient established by the dry air inside space 8 of the casing 1. Caps 13 and 14 provide a seal for the bores 20 of the hollow fiber membranes 2 when the device is not in use.

The casing of the device of the present invention can be made of any material inert and impervious to water vapor, for example, polypropylene or glass. The casing can be a rigid or flexible material. The shape of the casing can be circular, cylindrical, square, or any other shape as long as it encloses the membranes and provides the space necessary for a desiccant. As a personal monitoring device for industrial hygiene, it is preferred to use a casing with a size and shape which makes the device attachable to the person and portable.

The membrane should be of a size and shape suitable for being enclosed by a casing as described above. The membrane may be flat or tubular. The preferred membrane is of tubular form, particularly hollow fibers. Depending on the desired application, the thickness, length and number of hollow fibers will vary. A single hollow fiber or a plurality of hollow fibers can be used.

The material used for the membrane of the present invention should be permeable to water and impermeable to compounds of interest such as organics collected from a sample of air. It is not necessary for the membrane to be impermeable to all compounds other than water. The membrane should, however, be able to separate at least some water vapor from an air sample and leave at least some amount of the compound of interest to be measured in the air sample. Nafion ®, a perfluorosulfonic acid substituted polytetrafluoroethylene polymeric membrane developed by duPont, is satisfactorily used as the membrane for the device of the present invention. Some chemicals known in the art not to permeate through Nafion ® membrane are, for example, carbon monoxide, carbon dioxide, hydrogen chloride (halides), anhydrous ammonia, hydrocarbons, chlorinated solvents, formalin, sulfur compounds, hydrogen, chlorine, hydrogen chloride, methylene chloride and benzene. The polymer employed to form the Nafion ® membrane has the following structure:

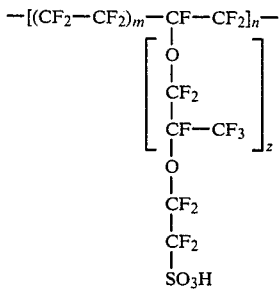

where m is an integer ranging from about 5 to about 13.5, z is an integer of 1 or greater and n is about 1000. A typical equivalent weight (EW) of the Nafion membrane used is from about 950 to about 1800 and a typical ion exchange capacity (IEC) of the membrane is from about 1.05 to about 0.55 milliequivalents per gram. A satisfactory membrane used according to the present invention contains an EW of about 1100 and an IEC of about 0.75.

The desiccant used in the present invention can be any material which adsorbs or absorbs water or water vapor. Examples of such materials are silica gel, calcium sulfate, and calcium chloride, suitably an indicating silica gel, i.e., a silica gel which undergoes a color change when it adsorbs water vapor, is used. The desiccant can be any shape or size compatible to the design of the casing, i.e., that will fit in the space between the inner surface of the casing and the outer side of the hollow fiber used. The amount of desiccant used will depend on the application of the device. For use as a personal monitoring device, the amount of desiccant used will be dependent on portability and the ability of the desiccant to keep the humidity of an air stream down to a desired level.

The device according to the present invention can be used for any application where at least partial removal of water from air is necessary or desired, for example, when used as a personal monitoring device as shown in FIG. 3. Referring to FIG. 3, one end section 3 or 4 of the device of the present invention 1 is open to the atmosphere. The other end section 3 or 4 of the device 1 is connected to one end of a sorbent tube 31 with adsorbent or absorbent material used for collecting selected chemicals from an air sample. The other end of the sorbent tube 31 is connected to a vacuum pump 33. Tygon ®, a vinyl compound manufactured by U.S. Stoneware Company, or rubber tubing 32 is suitably used to make the connections between the sorbent tube 31 and the device 1 and the sorbent tube 31 and the vacuum pump 33. The vacuum pump 33 is used for drawing air through the sorbent tube 31 and the device 1. The device 1 may be fastened to the outer garment of a person with a fastener means 34 such as a clip. The vacuum pump 33 can also be secured to a person by known means such as a belt case. In operation, an air sample is drawn through the device 1 which separates or removes at least a portion of the water vapor from the air sample before the air sample enters the sorbent tube 31. The air sample is then drawn through the sorbent tube which traps chemical vapors of interest. Thereafter, the air sample continues through an outlet in the vacuum pump 33.

As an exemplification of the present invention, device 1 is connected to a two section sorbent tube containing 520 mg of silica gel in the front section of the tube and 260 mg of silica gel in the back section of the tube. The sorbent tube is used for monitoring, for example, biphenyl. At an air sample flow rate of 150 cc/min for 8 hours, a 95 percent recovery of biphenyl is obtained without the occurrence of breakthrough in the sorbent tube. The above-mentioned sorbent tube and vacuum pump are well known in the art of air sampling. These instruments are commercially available, for example, from Environmental Compliance Corporation.

Another application in which the device of the present invention is useful is in combination with a portable or stationary vapor monitoring instrument, for example, a photoionization analyzer like the one described in the article by Driscoll, J. N. and Becker, J. H., "Industrial Hygiene Monitoring with a Variable Selectivity Photoionization Analyzer", American Laboratory, pages 69–76, November, 1979, which is incorporated herein by reference. The device of the present invention is connected to the sample inlet of the photoionization analyzer and removes water vapor from the sample prior to being measured by the analyzer.

To better illustrate the device of the present invention, the following examples were carried out using three different embodiments of the present invention. One embodiment, hereinafter referred to as Device A, has the configuration as shown in FIG. 1. The casing or housing was manufactured of glass at a glass laboratory by methods known in the art of glass making. The two cylindrical end sections were 0.5 inch in length and 3 millimeters (mm) in inside diameter each. The middle section was 4.5 inches in length and 11.6 mm in inside diameter.

The casing contained three Nafion ® #811X hollow fibers extending the length of the casing. The tubing size was 0.625 mm inside diameter and 0.875 mm outside diameter with a 10-mil wall thickness. The Nafion ® hollow fibers which had an equivalent weight of 1100 in H+ form, are manufactured by duPont.

A sealant, E-POX-E, available from Duro Loctite Corporation, which is an epoxy and polyamide resin, was used to seal the two end sections around the hollow fibers. The space formed between the outside of the hollow fibers and inner surface of the middle section of the casing was filled with approximately 10 grams of indicating silica gel, 6–16 mesh, in crystal form, blue in color which is available from MCA Chemicals, Inc. The silica gel was packed into the casing through the opening in the middle section of the casing which was subsequently sealed with a rubber cap.

Another embodiment was prepared according to the present invention, and is hereinafter referred to as Device B. It was identical to Device A except that the middle section was 2.0 inches in length instead of 4.5 inches, making the hollow fibers of Device B shorter than the hollow fibres of Device A.

A third embodiment was prepared and is hereinafter referred to as Device C. The casing or housing was formed of polypropylene cylinder with a top and bottom. The inside diameter of the cylinder was about 8 centimeters (cm) and the height of the cylinder was 4 cm. The top of the cylinder was removable. The side of the cylinder had two openings fitted with chromatograph end fittings of ⅛ inch outside diameter tubing, one opening being an inlet for the air sample and the other opening being an outlet for the air sample. Three Nafion ® #811X hollow fibers manufactured by duPont #811X, with an 1100 EW in H+ form were used in this device. The hollow fibers had a length of 2 feet and an inside diameter of 0.625 mm. Each end of the hollow fibers were molded into an ethylene/acrylic acid copolymer end fitting and thereafter connected to the inlet and outlet openings of the cylinder from within the cylinder. The hollow fibers were laid inside the cylinder in a loop to fit therein. The space outside the hollow fibers but within the casing was filled with desiccant, 6–16 mesh indicating silica gel. The top of the cylinder was secured with ⅜ inch screws.

EXAMPLES 1–3

Separation of water vapor from an air sample using the Device A above was performed under controlled conditions. One end of the device was connected to a Miller-Nelson humidity control system (HCS) unit, Model 201. The other end of the device was connected to a humidity sensor which was connected to a vacuum pump. All connections were made with Teflon ®, a tetrafluoroethylene fluorocarbon polymer manufactured by duPont and rubber tubing.

The Miller-Nelson HCS unit is capable of generating humidity conditions from 15 to 95 percent relative humidity (RH) and temperature conditions from ambient (about 68° F. to 95° F.) at sample air flow rates of up to about 100 liters per minute (1 pm). This unit is commercially available from Miller-Nelson Research, Inc. The Miller-Nelson HCS was equipped with an integral relative humidity and temperature sensor consisting of a General Eastern Model 400CD, which senses and digitally displays the conditions of the air stream as it exits the unit.

Employing the Miller-Nelson unit, a humid air sample at 90 percent RH and 74° F. was generated and drawn sequentially through the device and then through a second humidity sensor at different sample air flow rates for about 8 hours. The humidity sensor connected after the device is a commercially available sensor, by Thunder Scientific Corporation. This sensor was used to continuously monitor the dew point of the air exiting the device. The dew point was recorded at various points in time as described in Table I. Water vapor content or humidity of air can be expressed in a number of forms, including absolute humidity, mixing ratio, dew point, and relative humidity, which are readily convertible using a psychometric chart.

The identical experiment above conducted with Device A was conducted with Devices B and C. Tables I and II, below, show that a significant amount of the water vapor was separated and removed from the air sample for about 8 hours.

TABLE I

| Time | Dew Point (°F.) | | | |
| | at 250 cc/min | | at 670 cc/min | |
| (Hr) | Device A | Device B | Device A | Device B |
|---|---|---|---|---|
| 0 | 70.0 | 73.0 | 70.0 | 73.7 |
| 0.02 | 24.0 | 33.6 | 34.7 | 41.3 |
| 0.4 | 36.5 | 52.0 | 43.4 | 51.1 |
| 1 | 36.6 | 52.0 | 45.0 | 51.8 |
| 2 | 38.0 | 50.0 | 46.0 | 51.8 |
| 4 | 41.5 | 55.0 | 49.9 | 58.0* |
| 6 | 44.4 | 56.0 | 51.2* | 63.3* |
| 8 | 48.2 | 58.1 | 57.4* | 64.0* |

*Almost all of the silica gel in the device turned from a blue color to a pink color indicating saturation of the silica gel desiccant was reached.

TABLE II

| Time | Dew Point (°F.) for Device C | | |
| (Hr) | at 50 cc/min | at 250 cc/min | at 670 cc/min |
|---|---|---|---|
| 0 | 71.5 | 71.8 | 72 |
| 0.2 | 29 | 20.0 | 30 |
| 0.5 | 28 | 24.0 | 30 |
| 1 | 28 | 24.7 | 30 |
| 3 | 26 | 27.0 | 30 |
| 5 | 26 | 29.0 | 29 |
| 7 |  | 31.0 | 29 |
| 9 |  | 31.0 |  |

A typical sample air flow rate range used for industrial hygiene monitoring, is from about 50 to about 1000 lpm. Tables I and II, above, show that the flow rate slightly affects the ability of a device with shorter hollow fibers to separate water vapor from air, but primarily the flow rate affects the time the silica gel lasts.

COMPARATIVE EXAMPLES 1 AND 2

The identical equipment used in Examples 1–3 was used in this example. Devices A and B were used except that the desiccant was removed from within the casing. This experiment was conducted to compare the performance of Devices A and B containing no desiccant within the casing with Devices A and B containing a desiccant within the casing. A humid air sample at 90 percent RH and 74° F. was generated and drawn through Device A connected in series with a humidity sensor identically as described in Examples 1-3 at a sample air flow rate of 250 cubic centimeters per minute. This same experiment was conducted using Device B. The dew point was recorded at different points in time as described in Table III. Before beginning this experiment, the space inside the casing was purged with dry air at 70° F. and about 5 percent RH, e.g., for about 5 minutes to substantially dry the air space inside the casing. Table III shows that in a very short time the dew point increases rapidly because the water vapor concentration gradient across the membrane is decreased.

In general, for many industrial hygiene applications, problems due to high humidity can be cured by reducing humidity below 0.008 pound water per pound of dry air or a dew point below 60° F. which is less than 50 percent RH at 70° F. Table III shows that this maximum point is approximately reached in less time using Devices A and B without desiccant than using Devices A and B with a desiccant as described in Table I.

TABLE III

| Time | Dew Point (°F.) | |
|---|---|---|
| (Hr) | Device A | Device B |
| 0 | 71.5 | 71.5 |
| 0.02 | 46.3 | 50.5 |
| 0.08 | 46.1 | 61.8 |
| 0.25 | 57.8 | 67.4 |
| 0.35 | 66.5 | 68.2 |

COMPARATIVE EXAMPLES 3-8

To be useful for industrial hygiene air monitoring applications, the device of the present invention must remove water vapor from the air streams and not remove other compounds of interest in the air sample. The purpose of this experiment was to compare the percent recovery of organic vapors after passing through the device of the present invention with the percent recovery of organic vapors without the device of the present invention.

Standard solutions containing organic compounds described in Runs A-F in Table IV were placed in a glass U-tube wrapped with heating tape. The outlet of the U-tube was connected to a glass "Y" tube. One outlet of the "Y" tube was connected to a sorbent tube which was sequentially connected to a vacuum pump. The other outlet of the "Y" tube was connected to Device C which was sequentially connected to a sorbent tube and vacuum pump. All connections were made with rubber or Tygon ® tubing. The inlet of the U-tube was open to the atmosphere for air to be drawn through. Vapors were generated by heating the U-tube above the boiling point of the compounds tested. Air at ambient humidity condition or 40% RH at 74° F. was pulled through the U-tube with the vapors and then simultaneously through a pair of sorbent tubes containing suitable adsorbent material for the compound tested, at a rate of 100 cc/min for a period of 60 minutes. The organic compounds collected in the sorbent tube were desorbed with a suitable solvent and subsequently analyzed by gas chromatography with flame ionization or photoionization detectors, a method well known in the art. The results of this experiment are described in Table IV. Table IV shows that recoveries of aliphatic, aromatic, and chlorinated hydrocarbons were near 100%, except for very high boiling materials, which were probably lost by condensation or adsorption in the tubing. Polar organics, such as phenol, showed significant losses due to partial permeation through the Nafion ® hollow fibers.

TABLE IV

| Run No. | Compound | Weight Added (µg) | % Recovery* Comparison |
|---|---|---|---|
| A | n-ALKANES | | |
| | $C_7$ | 342 | 100 |
| | $C_8$ | 281 | 100 |
| | $C_9$ | 180 | 101 |
| | $C_{10}$ | 182 | 99 |
| | $C_{11}$ | 185 | 106 |
| | $C_{12}$ | 187 | 102 |
| | $C_{13}$ | 189 | 99 |
| | $C_{14}$ | 153 | 100 |
| | $C_{15}$ | 154 | 93 |
| | $C_{16}$ | 116 | 70 |
| | $C_{17}$ | 117 | 70 |
| B | 1-ALKENES | | |
| | $C_7$ | 349 | 100 |
| | $C_8$ | 286 | 100 |
| | $C_9$ | 183 | 101 |
| | $C_{10}$ | 185 | 101 |
| | $C_{11}$ | 188 | 102 |
| | $C_{12}$ | 189 | 100 |
| | $C_{13}$ | 192 | 98 |
| | $C_{14}$ | 155 | 92 |
| | $C_{15}$ | 156 | 82 |
| | $C_{16}$ | 117 | 88 |
| | $C_{17}$ | 118 | 89 |
| C | PHENOL | | |
| | Phenol | 154 | 43 |
| D | AROMATIC HYDROCARBONS | | |
| | Benzene | 396 | 100 |
| | Toluene | 390 | 102 |
| | Ethyl benzene | 390 | 103 |
| | n-Propyl benzene | 389 | 104 |
| | n-Butyl benzene | 387 | 100 |
| | n-Hexyl benzene | 389 | 103 |
| | n-Octyl benzene | 384 | 94 |
| | n-Decyl benzene | 394 | 46 |
| E | CHLOROBENZENES | | |
| | monochlorobenzene | 21.8 | 100 |
| | 1,3-dichlorobenzene | 25.4 | 100 |
| | 1,4-dichlorobenzene | 33.7 | 100 |
| | 1,2-dichlorobenzene | 25.9 | 100 |
| | 1,3,5-trichlorobenzene | 29.0 | 100 |
| | 1,2,4-trichlorobenzene | 28.5 | 102 |
| | 1,2,3-trichlorobenzene | 21.8 | 100 |
| | 1,2,4,5-tetrachlorobenzene | 35.5 | 100 |
| | 1,2,3,4-tetrachlorobenzene | 34.2 | 100 |
| | pentachlorobenzene | 42.9 | 100 |
| | hexachlorobenzene | 52.5 | 100 |
| F | OTHERS | | |
| | biphenyl | 994 | 91 |
| | phenyl ether | 312 | 86 |
| | 3-ethylbiphenyl | 565 | 44 |
| | 4-ethylbiphenyl | 755 | 36 |

*Recovery comparison is defined as
$$\frac{\% \text{ recovery with device of the present invention}}{\% \text{ recovery without device of the present invention}} \times 100$$

COMPARATIVE EXAMPLES 9-14

The purpose of this experiment was to demonstrate the separation of water vapor from an air stream containing organic vapors using a device of the present invention and to compare the recovery of the organic vapors in a sorbent tube preceded by a device of the present invention to the recovery of the organic vapors in a sorbent tube not preceded by a device of the present invention. The organic vapors tested were those which exhibited low recoveries or early breakthrough when collected in high humidity conditions in a sorbent tube. The collection of the organic vapors was tested under controlled conditions.

The Miller-Nelson humidity control system equipped with a General Eastern Model 400CD integral relative humidity and temperature sensor described in Example 1 was used to generate and monitor humid air conditions. The Miller-Nelson unit was connected to an apparatus for generating known concentrations of organic vapors. This apparatus is a Dynacalibrator Model 340-53-X with National Bureau of Standards certified permeation tubes manufactured by Metronics.

The Dynacalibrator unit was connected to a laboratory glass manifold with several outlets with stopcocks. To one outlet, a device of the present invention was connected which was sequentially connected to an adsorbent tube followed by a vacuum pump. To another outlet was connected a sorbent tube which was sequentially connected to a vacuum pump. All connections were made with rubber or Tygon ® tubing. With the laboratory set-up above, a stream of air containing water and organic vapors was simultaneously pulled through the sorbent tube, not preceded by a device of the present invention, and through a sorbent tube preceded by a device of the present invention.

In each of the following Runs A-F, air samples containing the organic compound of interest were drawn through the apparatus above with a commercially available vacuum pump.

Run A

Four samples of toluene as described in Table V were separately drawn through the apparatus described above. The concentration of each toluene sample in air was 11 parts per million (ppm), volume per volume (v/v) of air. Each sample was drawn through a 600 milligram (mg) charcoal adsorbent tube for a period of 90 minutes at a flow rate of 50 cubic centimeters per minute (cc/min). Device A was used for separating the water vapor from the sample. The results described in Table V show that the humidity in the air sample had no significant effect on the collectability of this compound.

Run B

Four samples of phenol as described in Table V were separately drawn through the apparatus described above. The concentration of each phenol sample was 1 ppm (v/v). Each sample was drawn through a 780 mg silica gel adsorbent tube for a period of 105 minutes at a flow rate of 100 cc/min. Device A was used for separating the water vapor from the samples. The results described in Table V show that humidity in the air sample has no significant effect on the collectability of phenol. However, phenol permeates significantly through the Nafion ® membrane of the device.

Run C

Four samples of ethylene oxide as described in Table V were separately drawn through the apparatus described above. The concentration of each ethylene oxide sample was 8 ppm (v/v). Each sample was drawn through a 1000 mg charcoal adsorbent tube for a period of 120 minutes at a flow rate of 50 cc/min. Device A was used for separating the water vapor from the samples. The test results for ethylene oxide as described in Table III show that the compound permeates significantly through the Nafion ® membrane of the device. However, the loss of compound due to the humidity in air without the device was much greater than with the device.

Run D

Four samples of methyl chloride as described in Table V were separately drawn through the apparatus described above. The concentration of each methyl chloride sample was 35 ppm (v/v). Each sample was drawn through a 600 mg charcoal adsorbent tube for a period of 250 minutes at a flow rate of 50 cc/min. Device A was used for separating the water vapor from the sample. The results described in Table V show that no methyl chloride was lost due to permeation through the Nafion ® tubing. However, the loss due to humidity was much greater without a device than with the device of the present invention.

Run E

Three samples of acrylonitrile as described in Table V were separately drawn through the apparatus described above. The concentration of each acrylonitrile sample was 5 ppm (v/v). Each sample was drawn through a 150 mg charcoal adsorbent tube for a period of 392 minutes at a flow rate of 100 cc/min. Device A was used for separating the water vapor from the samples. The results described in Table V show that breakthrough problems are eliminated and no loss of compound due to humidity results when a device of the present invention is used.

Run F

Four samples of a biphenyl and diphenyl ether (diphenyl oxide) mixture as described in Table V were separately drawn through the apparatus described above. Each sample of the mixture contained 0.01–0.3 ppm biphenyl and 0.02–0.6 ppm diphenyl oxide. Each sample was drawn through a 780 mg silica gel adsorbent tube for a period of 480 minutes at a flow rate of 150 cc/min. Device A was used in this experiment. The results described in Table V show that the breakthrough problem and loss of compound due to high humidity are eliminated when a device of the present invention is used.

TABLE V

| Run No. | Sample No. | Compound | % RH (At 74° F.) | Device Used? | Recovery[a] (%) | Breakthrough[b] (%) | Recovery Relative to Sample No. 1[c] (%) | Loss Due to High Humidity Relative to Sample No. 1 Without Device[d] (%) | Loss Due to High Humidity Relative to Sample No. 1 With Device[e] (%) | Loss Due to Permeation at 20% RH[f] (%) |
|---|---|---|---|---|---|---|---|---|---|---|
| A | 1 | toluene | 20 | No | 100 | 0 | 100 | 0 | 0 | 0 |
|   | 2 | toluene | 80 | No | 101 | 0 | 101 |   |   |   |
|   | 3 | toluene | 20 | Yes | 110 | 0 | 110 |   |   |   |
|   | 4 | toluene | 80 | Yes | 101 | 0 | 101 |   |   |   |
| B | 1 | phenol | 20 | No | 96 | 0 | 100 | 6 | 7 | 45 |

TABLE V-continued

| Run No. | Sample No. | Compound | % RH (At 74° F.) | Device Used? | Recovery[a] (%) | Breakthrough[b] (%) | Recovery Relative to Sample No. 1[c] (%) | Loss Due to High Humidity Relative to Sample No. 1 | | Loss Due to Permeation at 20% RH[f] (%) |
|---|---|---|---|---|---|---|---|---|---|---|
| | | | | | | | | Without Device[d] (%) | With Device[e] (%) | |
| | 2 | phenol | 80 | No | 90 | 0 | 94 | | | |
| | 3 | phenol | 20 | Yes | 53 | 0 | 55 | | | |
| | 4 | phenol | 80 | Yes | 46 | 0 | 48 | | | |
| C | 1 | ethylene oxide | 20 | No | 100 | 0 | 100 | 31 | 14 | 42 |
| | 2 | ethylene oxide | 80 | No | 69 | 0 | 69 | | | |
| | 3 | ethylene oxide | 20 | Yes | 58 | 0 | 58 | | | |
| | 4 | ethylene oxide | 80 | Yes | 44 | 0 | 44 | | | |
| D | 1 | methyl chloride | 20 | No | 67 | 33 | 100 | 35 | 2 | 0 |
| | 2 | methyl chloride | 80 | No | 32 | 32 | 48 | | | |
| | 3 | methyl chloride | 20 | Yes | 68 | 54 | 101 | | | |
| | 4 | methyl chloride | 80 | Yes | 66 | 30 | 99 | | | |
| E | 1 | acrylonitrile | 40 | No | 91 | 0 | 100 | 35 | 0 | 0 |
| | 2 | acrylonitrile | 95 | No | 65 | 33 | 65 | | | |
| | 4 | acrylonitrile | 95 | Yes | 93 | 0 | 100 | | | |
| F | 1 | biphenyl and diphenyl oxide | 40 | No | 100 | 0 | 100 | 50 | 0 | 5 |
| | 2 | biphenyl and diphenyl oxide | 80 | No | 50 | 90 | 50 | | | |
| | 3 | biphenyl and diphenyl oxide | 40 | Yes | 95 | 0 | 95 | | | |
| | 4 | biphenyl and diphenyl oxide | 80 | Yes | 97 | 0 | 97 | | | |

Notes

[a] % Recovery = $\frac{\text{concentration found on sorbent tube sections}}{\text{concentration added to the sample}} \times 100$

[b] % Breakthrough = $\frac{\text{concentration found on back section of sorbent tube}}{\text{total concentration found on front and back sections of the sorbent tube}} \times 100$

[c] % Recovery Relative to Sample No. 1 = $\frac{\text{\% recovery for sample \#x}}{\text{\% recovery for sample \#1}} \times 100$ for each run.

[d] % Loss due to high humidity without device of the present invention = % Recovery Relative to Sample No. 1 for sample No 1 − % Recovery Relative to Sample No. 1 for sample No. 2 in each run.

[e] % Loss due to high humidity with device of the present invention = % Recovery Relative to Sample No 1 for sample No. 3 − % Recovery Relative to Sample No. 1 for sample No. 4 in each run.

[f] % Loss due to permeation of organic vapor through device of the present invention at 20% RH = % Recovery Relative to Sample No. 1 for sample No. 1 − % Recovery Relative to Sample No. 1 for sample No. 3 in each run.

It is to be understood that the present invention should not be limited to the specific embodiments herein stated. It will be apparent to those skilled in the art that various changes in the details, materials and arrangements of parts which have been herein described and illustrated in order to explain the nature of the invention can be made within the principle and scope of the invention as expressed in the appended claims.

What is claimed is:

1. A method of separating water vapor from air comprising contacting the first side of a water permeable membrane with air whereby the water vapor permeates from the first side of the membrane to the second side, said water permeable membrane being enclosed in a casing containing a desiccant between the second side of the membrane and inside surface of the casing.

2. The method in claim 1 wherein the membrane means is a hollow fiber.

3. The method in claims 1 or 2 wherein the membrane means is a perfluorosulfonic acid substituted polytetrafluoroethylene polymer.

4. A method of dehumidifying an air sample containing organic vapors comprising the following steps in sequence:
 (a) connecting a water vapor separating device to a sorbent tube, said water vapor separating device comprising a casing means containing
  (i) a water permeable membrane with a first and second side,
  (ii) a desiccant between the second side of the membrane and inner surface of the casing; and
 (b) drawing an air sample through the water vapor separating device and sorbent tube.

5. The method in claim 4 wherein the membrane means is a hollow fiber.

6. The method in claims 4 or 5 wherein the membrane means is a perfluorosulfonic acid substituted polytetrafluoroethylene polymer.

7. In a method for sampling chemical vapors in the industrial atmosphere, including passing a sample of air through a sorbent tube, the improvement which comprises passing a sample of air through a device for separating at least a portion of water vapor from the air sample prior to the sorbent tube said device having a desiccant.

8. In an apparatus for sampling chemical vapors in the industrial atmosphere, including a pump means and a sorbent tube, the improvement which comprises a device for separating at least a portion of water vapor from an air sample connected to the sorbent tube said device having a desiccant.

9. A device for separating water vapor from an air sample comprising a casing means of water vapor impermeable material containing
  (a) at least one membrane means of water vapor permeable material with a first and second side,
    the membrane means adapted for selectively permeating water vapor through the wall of the membrane means,
    the membrane means being positioned in the casing means to form a first space and a second space within the casing means,
    the first and second spaces of the casing means communicating with each other through the wall of the membrane means,
    the second space adapted for contacting an air sample containing water vapor with the second side of the membrane means, such that at least a portion of the water vapor present in the air sample permeates through the wall of the membrane means to the first space, and
  (b) a desiccant occupying the first space of the casing means.

10. The device in claim 9 wherein the membrane means is a hollow fiber.

11. The device in claims 9 or 10 wherein the membrane means is a perfluorosulfonic acid substituted polytetrafluoroethylene polymer.

12. A portable air sampling device comprising:
  a first casing means of water vapor impermeable material containing a water vapor permeable membrane with a first and second side, and a desiccant between the second side of the membrane and inner surface of the first casing; and a second casing means containing sorbent material communicating with the first side of the membrane of the first casing.

13. The device in claim 12 wherein the membrane means is a hollow fiber.

14. The device in claims 12 or 13 wherein the membrane means is a perfluorosulfonic acid substituted polytetrafluoroethylene polymer.

15. A device for separating water vapor from an air sample comprising a casing means of water vapor impermeable material with a plurality of hollow fiber membranes extending through the casing means,
  the hollow fibers adapted for selectively permeating water vapor through the wall of the hollow fibers,
  the hollow fibers having an inlet and an outlet for passing an air sample through the bores of the hollow fibers, and
  a desiccant at least partially surrounding the hollow fibers, the desiccant being enclosed by the casing means.

16. The device of claim 15 wherein the hollow fibers are made of a perfluorosulfonic acid substituted polytetrafluoroethylene polymer.

17. A method of separating water vapor from an air sample comprising passing an air sample through the water vapor separating device of claim 9.

18. A method of separating water vapor from an air sample comprising passing an air sample through the water vapor separating device of claim 15.

* * * * *